(12) United States Patent
Cottrell et al.

(10) Patent No.: US 7,368,435 B2
(45) Date of Patent: May 6, 2008

(54) TOPICAL ENDOPARASITICIDE AND ECTOPARASITICIDE FORMULATIONS

(75) Inventors: Ian W. Cottrell, Basking Ridge, NJ (US); Albert Ahn, Short Hills, NJ (US); Richard Fisher, Brookville, OH (US)

(73) Assignee: Summit Vetpharm, LLC, Fort Lee, NJ (US)

( * ) Notice: Subject to any disclaimer, the term of this patent is extended or adjusted under 35 U.S.C. 154(b) by 116 days.

(21) Appl. No.: 11/221,654

(22) Filed: Sep. 7, 2005

(65) Prior Publication Data

US 2006/0062817 A1   Mar. 23, 2006

Related U.S. Application Data

(63) Continuation-in-part of application No. 11/181,344, filed on Jul. 14, 2005, which is a continuation-in-part of application No. 10/910,542, filed on Aug. 3, 2004, and a continuation-in-part of application No. 10/242,551, filed on Sep. 12, 2002, now Pat. No. 6,867,223.

(60) Provisional application No. 60/607,900, filed on Sep. 8, 2004, provisional application No. 60/493,976, filed on Aug. 8, 2003, provisional application No. 60/554,563, filed on Mar. 19, 2004.

(51) Int. Cl.
| | |
|---|---|
| A61K 31/215 | (2006.01) |
| A61K 31/341 | (2006.01) |
| A61K 31/4402 | (2006.01) |
| A61K 31/231 | (2006.01) |
| A61K 31/7042 | (2006.01) |
| A61K 31/7048 | (2006.01) |
| A61P 33/00 | (2006.01) |
| A61P 33/10 | (2006.01) |
| A61P 33/14 | (2006.01) |

(52) U.S. Cl. .............. 514/30; 514/345; 514/471; 514/531; 514/549; 514/552; 514/875; 514/970

(58) Field of Classification Search ................ 514/345, 514/471, 531, 549, 552, 875, 970, 30
See application file for complete search history.

(56) References Cited

U.S. PATENT DOCUMENTS

| | | | |
|---|---|---|---|
| 5,434,181 A | | 7/1995 | Kodaka et al. |
| 5,439,924 A | * | 8/1995 | Miller ................. 514/345 |
| 5,532,365 A | | 7/1996 | Kodaka et al. |
| 6,013,636 A | * | 1/2000 | Harvey ................. 514/30 |
| 6,096,329 A | | 8/2000 | Jeannin |
| 6,200,973 B1 | | 3/2001 | Sembo et al. |
| 6,201,017 B1 | * | 3/2001 | Sembo et al. ............. 514/471 |
| 6,274,570 B1 | | 8/2001 | Vogt et al. |
| 6,479,542 B2 | | 11/2002 | Sembo et al. |
| 6,566,392 B1 | | 5/2003 | Okada et al. |
| 6,588,374 B1 | | 7/2003 | Cottrell et al. |
| 6,663,876 B2 | | 12/2003 | Campbell et al. |
| 6,814,030 B2 | | 11/2004 | Cottrell et al. |
| 6,867,223 B2 | | 3/2005 | Cottrell et al. |
| 6,889,632 B2 | | 5/2005 | Cottrell et al. |
| 2003/0013684 A1 | | 1/2003 | Kawahara et al. |
| 2005/0009880 A1 | | 1/2005 | Cottrell et al. |
| 2005/0009881 A1 | | 1/2005 | Cottrell et al. |
| 2005/0096386 A1 | | 5/2005 | Cottrell et al. |

FOREIGN PATENT DOCUMENTS

| | | | |
|---|---|---|---|
| EP | 0 979 606 A1 | | 2/2000 |
| EP | 976328 | * | 2/2000 |
| JP | 3-220176 | | 9/1991 |
| WO | WO 02/05639 A2 | | 1/2002 |

OTHER PUBLICATIONS

Webster's New World Dictionary, Simon & Schuster, New York, 1988, p. 1067.*
HCAPLUS abstract 2005:1058408 (2005).*
HCAPLUS abstract 2005:1058409 (2005).*
Bishop, B.F. et al., "Selamectin: a novel broad-spectrum endectocide for dogs and cats," Veterinary Parasitology, vol. 91, pp. 163-176 (2000).*
Hackh's Chemical Dictionary, 4th ed., McGraw-Hill Book Co., New York, p. 400, definition of "macrocyclic."*

* cited by examiner

*Primary Examiner*—John Pak
(74) *Attorney, Agent, or Firm*—Stroock, Stroock & Lavan LLP

(57) ABSTRACT

A topical formulation having significant parasiticidal activity effective against endoparasites and/or ectoparasites such as heartworms, mites, fleas, ticks, flies is provided, which can be safe to use and avoids the many common deleterious side effects of conventional topical formulations. The topical formulations comprise a combination of a macrocyclic lactone, a neo-nicotinoid and optionally, an insect growth regulator. The topical formulation can be packaged together or packaged so that the macrocyclic lactone and the neo-nicotinoid are stored separately prior to administering the topical insecticide formulation to the animal.

10 Claims, No Drawings

TOPICAL ENDOPARASITICIDE AND ECTOPARASITICIDE FORMULATIONS

This application claims the benefit of U.S. Provisional Application No. 60/607,900, filed Sep. 8, 2004, and is a continuation-in-part of U.S. application Ser. No. 11/181,344, filed Jul. 14, 2005, which is a continuation-in-part of and claims priority to U.S. application Ser. No. 10/910,542, filed Aug. 3, 2004, which claims priority benefit to U.S. Provisional Application No. 60/493,976, filed Aug. 8, 2003, and U.S. Provisional Application No. 60/554,563, filed Mar. 19, 2004, and is also a continuation-in-part of U.S. application Ser. No. 10/242,551, filed Sep. 12, 2002, now U.S. Pat. No. 6,867,223, the contents of all of which are incorporated herein by reference.

BACKGROUND OF INVENTION

This invention relates generally to topical formulations that can have significant parasiticidal activity as insecticides, endoparasites, ectoparasiticides and acaricides in animal health, such as one suitable to use on house pets such as dogs and cats.

The infestation of companion animals with endoparasites and/or ectoparasites such as heartworms, roundworms, hookworms, whipworms, fleas, ticks, flies, mites and the like is highly undesirable and as such, it is beneficial to include multiple pharmaceutical drugs in the same formulation in order to target a wider variety of parasites. Additionally, it has become common to administer both topical and internal insecticides to livestock and pets. Topical applications can be desirable since many formulations are acceptably safe when used topically, but not when used internally.

However, various topical pharmaceutical formulations have drawbacks. Some formulations require a large volume to be applied to the animal. This can cause considerable mess and can lead to an unpleasant smell. Additionally, if the dosage of a topical formulation is in a large volume, it can be easily shaken off by the animal thereby reducing the effectiveness of the formulation. Also, when the animal is a house pet, there is a further complication in that the formulation should be safe for human contact. It should also not lead to staining of furniture, carpeting and the like. Finally, even if safe, topical formulations should not be irritating or lead to rashes, hair loss or exhibit other unpleasant side effects.

There is therefore a need for an improved topical formulation for the treatment of endoparasites and ectoparasites that overcomes drawbacks of the prior art.

SUMMARY OF THE INVENTION

Generally speaking, in accordance with the invention, a topical pharmaceutical formulation comprising a macrocyclic lactone, together with a neo-nicotinoid and/or an insect growth regulator, particularly one for use on cats and dogs, is provided. Formulations in accordance with the invention can be safe to use and avoids many common deleterious side effects of conventional topical formulations.

The invention provides a topical formulation that contains a combination of insecticides and insect growth regulators, which can be effective to kill endoparasites and ectoparasites such as heartworm, fleas, flea eggs, flea larvae, ticks, tick eggs, tick larvae, tick nymphs, mites and mosquitoes. The selection of the combination of insecticides and insect growth regulators produces a composition having high parasitical activity, thereby providing broad protection against a variety of endoparasites and ectoparasites with a single application of the topical formulation. The compositions derived herein can also be useful to improve the speed of result and decrease the reoccurrence, compared to other formulations.

The invention provides a topical formulation that contains a combination of a first active ingredient comprising a macrocyclic lactone and a second active ingredient comprising a neo-nicotinoid. Preferably, the topical formulation further contains an insect growth regulator (IGR). In a preferred embodiment of the invention, the macrocyclic lactone in the composition comprises at least one of ivermectin, selamectin, doramectin, moxidectin or eprinomectin. The neo-nicotinoid can comprise a (tetrahydro-3-furanyl)methylamine derivative of formula (1), as identified below. In another embodiment of the invention, the neo-nicotinoid comprises a chloronicotinyl insecticide, preferably acetamiprid. The insect growth regulator (IGR) preferably comprises pyriproxyfen and/or methoprene. As used herein, the identification of an active ingredient, e.g., ivermectin, is intended to also refer to other pharmaceutically active forms of the active ingredient, such as esters, salts, hydrochlorides, acid or base forms, isomers and so forth.

In another embodiment of the invention, the topical formulation also contains a pyrethroid such as permethrin or phenothrin in order to provide additional acaricide efficacy and to repel and kill mosquitoes.

It has been determined that it is difficult to form a high concentration of dinotefuran or acetamiprid and permethrin or phenothrin, and it is likely to result in a solution that can be unstable when stored at room temperature for reasonable amounts of time. Therefore, it has been found preferable to produce a first formulation comprising a macrocyclic lactone and a neo-nicotinoid and a second formulation comprising permethrin or phenothrin, and to keep these formulations separated until prior to, preferably immediately prior to application. Preferably, topical formulation also contains an IGR, which may be packaged with either the first or second formulation or in yet another container.

The first and second formulations are advantageously produced and packaged in a manner so that the first and second formulations can be prevented from interacting prior to application of the formulation to the animal. Preferably, the first and second formulations can be stored separately from each other in a package or container having two associated, preferably attached, but individual chambers to prevent the mixing of the first and second formulations prior to administration of the first and second formulation to the animal. The first and second formulations can be advantageously packaged in a container or chamber that is opaque in order to prevent the photodegradation of the active ingredients in the formulations. Prior to administration, the packages containing the first and second formulations in their respective separate chambers are opened, and the first and second formulations are dispensed simultaneously or at least at about the same time, to the animal.

Accordingly, it is an object of the invention to provide an improved topical formulation that is effective against a variety of parasites.

Another object of the invention is to provide a method for controlling parasites.

Another object of the invention is to provide a topical formulation that works more rapidly and/or more permanently than other topical formulations.

Another object of the invention is to provide an improved method of making an insecticide.

Another object of the invention is to provide a new insecticide packaging system.

Other objects and features will be in part apparent and in part pointed out.

DETAILED DESCRIPTION OF THE PREFERRED EMBODIMENTS

In accordance with the invention, insecticidal compositions are provided which contain a combination of a macrocyclic lactone, a neo-nicotinoid and preferably, an insect growth regulator, that are effective against endoparasites and ectoparasites such as heartworm, fleas, flea eggs, ticks, and mites. The combination of active ingredients produces topical formulations that provides broad protection against endoparasites and ectoparasites using a single application of the formulation.

Preferably, insecticidal compositions of the invention comprise a first active ingredient comprising a macrocyclic lactone such as ivermectin, selamectin, doramectin, moxidectin or eprinomectin, combined with a second active ingredient comprising a neo-nicotinoid such as dinotefuran or acetamiprid, in a suitable solvent solution. It should be noted that in embodiments where the first active ingredient is dinotefuran and the second active ingredient is acetamiprid, a solvent comprising ethyl lactate and water should not be utilized. Rather, it has been determined that an effective solvent for the solubilization of high concentrations of dinotefuran and acetamiprid comprises ethanol.

The treatment of different endoparasites and ectoparasites can be targeted by including a particular macrocyclic lactone in the formulation. Accordingly, in preferred embodiments of the invention, the topical formulation further comprises an insect growth regulator (IGR). The combination of the macrocyclic lactone and the neo-nicotinoid with an IGR preferably results in a topical formulation having effective insecticidal activity against e.g., flea larvae and flea eggs.

In one preferred embodiment of the invention, the first component in the formulation comprises a macrocyclic lactone such as ivermectin, selamectin, doramectin, moxidectin or eprinomectin, the second component is dinotefuran or N-((6-chloro-3-pyridinyl)methyl)-N'-cyano-N-methyl-ethanimidamide (acetamiprid), and the IGR is pyriproxyfen and/or methoprene.

In another preferred embodiment of the invention, the macrocyclic lactone in the formulation comprises at least one of ivermectin, selamectin, doramectin, moxidectin and eprinomectin, the neo-nicotinoid comprises a (tetrahydro-3-furanyl)methylamine derivative of following formula (1), and the IGR comprises pyriproxyfen and/or methoprene. The (tetrahydro-3-furanyl)methylamine derivatives of the formula (1) have an excellent insecticidal activity even in the absence of a pyridylmethyl group or a thiazolylmethyl group in their molecular structure.

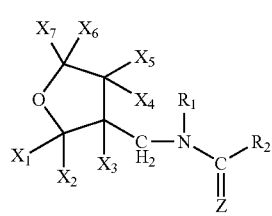

Formula (1)

where $X_1$, $X_2$, $X_3$, $X_4$, $X_5$, $X_6$ and $X_7$ each represent each a hydrogen atom or an alkyl group having from 1 to 4 carbon atoms; $R_1$ represents a hydrogen atom, an alkyl group having from 1 to 5 carbon atoms, an alkenyl group having 3 carbon atoms, a benzyl group, an alkoxyalkyl group having from 2 to 4 carbon atoms (in its whole group), an alkyloxycarbonyl group having from 1 to 3 carbon atoms, a phenoxy carbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group or an N,N-dimethylcarbamoyl group; $R_2$ represents a hydrogen atom, an amino group, a methyl group, an alkylamino group having from 1 to 5 carbon atoms, a di-substituted alkylamino group having from 2 to 5 carbon atoms (in its whole group), a 1-pyrrolidinyl group, an alkenylamino group having 3 carbon atoms, an alkynylamino group having 3 carbon atoms, a methoxyamino group, an alkoxyalkylamino group having from 2 to 4 carbon atoms (in its whole group), a methylthio group or —N($Y_1$)$Y_2$ (where $Y_1$ represents an alkyloxycarbonyl group having from 1 to 3 carbon atoms, a phenoxycarbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group, an N,N-dimethylcarbamoyl group, a (tetrahydro-3-furanyl) methyl group or a benzyl group, and $Y_2$ represents a hydrogen atom or an alkyl group having from 1 to 5 carbon atoms); and Z represents =N—$NO_2$, =CH—$NO_2$ or =N—CN.

Intermediates for producing the compounds of the formula (1) are represented by a formula (2):

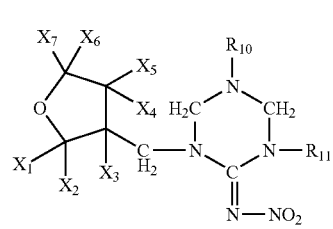

Formula (2)

where $X_1$, $X_2$, $X_3$, $X_4$, $X_5$, $X_6$ and $X_7$ each represent each a hydrogen atom or an alkyl group having from 1 to 4 carbon atoms; $R_{10}$ represents an alkyl group having from 1 to 5 carbon atoms or a benzyl group; and $R_{11}$ represents an alkyl group having from 1 to 5 carbon atoms or a benzyl group.

The (tetrahydro-3-furanyl)methylamine derivatives of the formula (1) and formula (2) according to the invention are excellent compounds having a high insecticidal activity and broad insecticidal spectrum. Further, agricultural chemicals containing the (tetrahydro-3-furanyl)methylamine derivatives of formula (1) and (2) according to the invention have outstanding characteristics as insecticides and hence are useful.

Specific examples of the alkyl group for $X_1$, $X_2$, $X_3$, $X_4$, $X_5$, $X_6$ and $X_7$ in the above formulae (1) and (2) include a methyl group, an ethyl group, an n-propyl group, an iso-propyl group, a tert-butyl group, and the like, preferably a methyl group.

Specific examples of the alkyl group for $R_1$ include a methyl group, an ethyl group, an n-propyl group, an iso-propyl group, an n-butyl group, an iso-butyl group, a sec-butyl group, a tert-butyl group, an n-pentyl group, and the like.

Specific examples of the alkenyl group for $R_1$ include a 1-propenyl group, a 2-propenyl group, and the like.

Specific examples of the alkoxyalkyl group for $R_1$ include a methoxymethyl group, an ethoxymethyl group, an n-propoxymethyl group, an iso-propoxymethyl group, a methoxyethyl group, an ethoxyethyl group, and the like.

Specific examples of the alkyloxycarbonyl group for $R_1$ include a methyloxycarbonyl group, an ethyloxycarbonyl group, an n-propyloxycarbonyl group, an iso-propyloxycarbonyl group, and the like.

Specific examples of the alkylcarbonyl group for $R_1$ include a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group, a tert-butylcarbonyl group, an n-pentylcarbonyl group, an n-hexylcarbonyl group, and the like.

Specific examples of the alkenylcarbonyl group for $R_1$ include a vinylcarbonyl group, a 1-methylvinylcarbonyl group, and the like.

Specific examples of the cycloalkylcarbonyl group for $R_1$ include a cyclopropylcarbonyl group, a cyclobutylcarbonyl group, a cyclopentylcarbonyl group, a cyclohexylcarbonyl group, and the like.

Specific examples of the benzoyl group substituted by alkyl group(s) for $R_1$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) for $R_1$ include a 2-chlorobenzoyl group, a 3-chlorobenzoyl group, a 4-chlorobenzoyl group, a 3,4-dichloro-benzoyl group, a 4-fluorobenzoyl group, and the like.

Although $R_1$ can take various substituents as described above, it is preferably a hydrogen atom, an alkylcarbonyl group having from 1 to 4 carbon atoms or a cyclopropyl-carbonyl group.

Specific examples of the alkylamino group for $R_2$ include a methylamino group, an ethylamino group, an n-propyl-amino group, an iso-propylamino group, an n-butylamino group, an iso-butylamino group, a sec-butylamino group, a tert-butylamino group, an n-pentylamino group, and the like, preferably a methylamino group.

Specific examples of the di-substituted alkylamino group for $R_2$ include a dimethylamino group, a diethylamino group, an N-methyl-N-ethylamino group, an N-methyl-N-n-propylamino group, an N-methyl-N-n-butylamino group, and the like, preferably a dimethylamino group.

Specific examples of the alkenylamino group for $R_2$ include a 1-propenylamino group, a 2-propenylamino group, and the like.

Specific examples of the alkynylamino group for $R_2$ include a propargylamino group, and the like.

Specific examples of the alkoxyalkylamino group for $R_2$ include a methoxymethylamino group, an ethoxymethylamino group, an n-propoxymethylamino group, an iso-propoxymethylamino group, a methoxyethylamino group, an ethoxyethylamino group, and the like.

Specific examples of the alkyloxycarbonyl group denoted by $Y_1$ for $R_2$ include a methyloxycarbonyl group, an ethyloxy-carbonyl group, an n-propyloxycarbonyl group, an iso-propyloxy-carbonyl group, and the like.

Specific examples of the alkylcarbonyl group denoted by $Y_1$ for $R_2$ include a methylcarbonyl group, an ethylcarbonyl group, an n-propylcarbonyl group, an iso-propylcarbonyl group, an n-butylcarbonyl group, an isobutylcarbonyl group, a sec-butyl-carbonyl group, a tertbutylcarbonyl group, an n-pentylcarbonyl group, an n-hexylcarbonyl group, and the like, preferably a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group and a tert-butylcarbonyl group.

Specific examples of the alkenylcarbonyl group denoted by $Y_1$ for $R_2$ include a vinylcarbonyl group, a 1-methyl-vinylcarbonyl group, and the like.

Specific examples of the cycloalkylcarbonyl group denoted by $Y_1$ for $R_2$ include a cyclopropylcarbonyl group, a cyclobutylcarbonyl group, a cyclopentylcarbonyl group, a cyclo-hexylcarbonyl group, and the like, preferably a cyclopropyl-carbonyl group.

Specific examples of the benzoyl group substituted byalkyl group(s) denoted by $Y_1$ for $R_2$ include a 2-methyl-benzoyl group, a 3-methylbenzoyl group, a 4-methylbenzoyl group, a 4-tert-butylbenzoyl group, and the like.

Specific examples of the benzoyl group substituted by halogen atom(s) denoted by $Y_1$ for $R_2$ include a 2-chlorobenzoyl group, a 3-chlorobenzoyl group, a 4-chlorobenzoyl group, a 3,4-dichlorobenzoyl group, a 4-fluoro benzoyl group, and the like.

Specific examples of the alkyl group denoted by $Y_2$ for $R_2$ include a methyl group, an ethyl group, an n-propyl group, an iso-propyl group, an n-butyl group, an iso-butyl group, a sec-butyl group, a tert-butyl group, an n-pentyl group, and the like, preferably a methyl group.

In the formula (1), compounds in which $R_1$ and $Y_1$ are concurrently an alkylcarbonyl group having from 1 to 4 carbon atoms or a cyclopropylcarbonyl group are preferred from the viewpoint of both insecticidal activity and production method.

In a preferred embodiment of the invention, the macrocyclic lactone comprises at least one ivermectin, selamectin, doramectin, moxidectin or eprinomectin, the neo-nicotinoid comprises 1-{(tetrahydro-3-furanyl)methyl}-2-nitro-3-methylguanidine (dinotefuran), and the insect growth regulator preferably comprises pyriproxyfen or methoprene. Dinotefuran is an insecticide that kills adult fleas, and pyriproxyfen and methoprene are insect growth regulators that kill flea larvae and prevent flea eggs from hatching. Accordingly, the combination of dinotefuran and an IGR such as pyriproxyfen or methoprene provides for an effective flea control system since only about 5% of the existing fleas on an animal are adults and the other 95% are in a juvenile state (eggs and larvae).

It has been determined that it is advantageous to dissolve or otherwise put the actives into a liquid form for use as a topical spot products on animals. It is of course, to be understood that in certain embodiments of the invention, it may be advantageous to isolate the actives, such as by granulation (e.g., spray granulation), encapsulation, use of micelles, encapsulated microbeads and the like. Topical spot products are more advantageous if the amount of liquid applied to the animal can be minimized. This should be balanced with the need for appropriate dosage to achieve the desired pesticidal effect. Therefore, it is desirable to include a high concentration of insecticide so that the total volume of the insecticide applied to the animal can be minimized.

Preferably, dinotefuran is dissolved in the formulation to a concentration of approximately 50 to 150 mg/ml, more preferably 100 to 150 mg/ml, and most preferably, approximately 150 mg/ml. Dinotefuran may be dissolved in particularly effective solvent systems such as a combination of water and ethanol or isopropanol, as disclosed in pending U.S. Ser. No. 10/242,552 filed on Sep. 12, 2002, now U.S. Pat. No. 6,814,030, or in phenyl methanol or ethanol, as disclosed in U.S. Pat. No. 6,588,374, or in ethyl lactate and water combinations. The contents of these references are incorporated herein by reference.

The treatment of different endoparasites and ectoparasites are targeted by including particular macrocyclic lactones specific for the target endoparasite or ectoparasite in the topical formulation. The combination of the macrocyclic lactone and neo-nicotinoid with an insect growth regulator preferably results in a topical formulation having effective insecticidal and parasiticidal activity against a variety of endoparasites and ectoparasites.

In another preferred embodiment of the invention, the topical formulation comprises a pyrethroid such as 2,2-Dimethyl-3-(2-methyl-1-propenyl)cyclopropanecarboxylic acid, (3-phenoxyphenyl)methyl ester (phenothrin) or cyclopropanecarboxylic acid, 3-(2,2-dichlorethenyl)-2,2-dimethyl-(3-phenoxyphenyl)methyl ester (permethrin) in order to provide additional acaricide efficacy and to repel and kill mosquitoes. Compositions containing permethrin in accordance with the invention are particularly advantageous for use on dogs, compared to their use on cats.

It has been determined that it is difficult to form a high concentration of dinotefuran or acetamiprid and permethrin or phenothrin, and it is likely to result in a solution that can be unstable when stored at room temperature for reasonable amounts of time. Therefore, it has been found preferable to produce a first formulation comprising a macrocyclic lactone and a neo-nicotinoid and a second formulation comprising permethrin or phenothrin. Preferably, the topical formulation further comprises an IGR, which can be included in the first or second formulation or even separately in yet another container. The first and second formulations are produced and packaged in a manner so that the first and second formulations are not permitted to interact prior to application of the total formulation to the animal. In one preferred embodiment of the invention, the first and second formulations are stored separately from each other in a package or container having two associated, preferably attached, but individual, chambers to prevent the mixing of the first and second formulations prior to administration of the first and second formulation to the animal.

It should be noted that in embodiments where the formulation is packaged using separate chambers or containers, the percentage of an active ingredient provided is the percentage of that active ingredient in a single solution. For example, 1 to 2% pyriproxyfen is the concentration of pyriproxyfen contained in the formulation in a single chamber rather than the concentration of pyriproxyfen in the total formulation of the combined chambers.

Macrocyclic lactones can be unstable in both acidic and basic solutions. For example, ivermectin is hygroscopic and therefore tends to be undesirably unstable. It has also been seen that macrocyclic lactones such as ivermectin are unstable in both acidic and basic solutions and are susceptible to photodegradation and oxidative degradation. Accordingly, in embodiments where the first active ingredient of the composition comprises ivermectin, it is preferable that the first and second formulations are stored in an opaque package or container to prevent the photodegradation of ivermectin during storage of the formulation. Even more preferably, the formulation will further comprise an antioxidant such as 2,6 ditertiarybutyl-4-methyl phenol (BHT) to prevent the oxidative degradation of ivermectin during storage of the formulation for a reasonable amount of time.

Prior to administration, the packages containing the first and second formulations in their respective separate chambers are opened, and the first and second formulations are dispensed simultaneously or at least at about the same time to the animal.

In one preferred embodiment of the invention, the first and second formulations can be packaged in a container having two associated, preferably attached, but individual, chambers to prevent the mixing of the formulations prior to the administration of the first and second formulations to the animal. Prior to administration, the container can be opened and the first and second formulations can be dispensed simultaneously or nearly simultaneously to the companion animal.

In another preferred embodiment of the invention, the insecticide composition of the invention can be packaged in a single dose package. Single dose containers make storage and disposal more convenient for animal owners. Preferably, the composition is packaged in a container encompassing two associated, preferably attached but individual chambers, which are separated by a barrier, preferably plastic, plastic coated paper or metal, such as aluminum foil. In one preferred embodiment of the invention, the first chamber and the second chamber are plastic tubes that are separate but fused together. In another embodiment of the invention, the first and second chambers are comprised of opaque plastic in order to prevent the photodegradation of the actives in the formulation.

During packaging, the first formulation, preferably comprising a macrocyclic lactone such as ivermectin, selamectin, doramectin, moxidectin or eprinomectin and a neo-nicotinoid, preferably dinotefuran or acetamiprid can be placed in the first chamber. The second formulation, preferably comprising permethrin or phenothrin can be placed in the second chamber. The topical formulation further comprises an IGR such as pyriproxyfen or methoprene, which may be included in the first or second formulation or in yet another container. Preferably, the first and second chambers can be separated by a barrier that prevents the interaction of the first and second formulations.

The entire container containing the first and second formulations in separate chambers is sealed, preferably with a tab or top, for use in opening the container prior to administration. After the container is sealed, the topical formulation can be safely stored in the container until administration of the formulation to the animal.

Prior to administration of the formulation to the animal, the container is opened by removing the tab or top. In one embodiment of the invention, the container is opened by twisting the tab thereby resulting in breaking or tearing of the barrier separating the two chambers, thereby allowing the first and second formulations to mix prior to administration of the insecticide formulation to the animal. After the two formulations are mixed, the two formulations are dispensed by squeezing or collapsing the body of the container either simultaneously or sequentially. In another embodiment of the invention, a dual plunger system can be employed to administer the formulation onto the animal.

It is of course understood that the first and second formulations need not be mixed together prior to administration of the topical formulation to the animal. Accordingly, in another embodiment of the invention, opening of the dual-chamber container does not result in the mixing of the first and second formulations. Rather, after the container is opened, the first and second formulations are dispensed onto the animal by squeezing or collapsing the container or containers, either simultaneously or sequentially.

In one embodiment of the invention, the formulation is packaged with instructions, advising to mix the formulations. In other embodiments, the instructions will direct the user not to mix the formulation upon application. Because compositions in accordance with preferred embodiments of the invention can be formulated with a relatively high concentration of active ingredients, a relatively small application of a spot or line on the animal can effectively prevent and control endoparasite and ectoparasite infestation on the animal for approximately one to four weeks post-administration. Preferably, the topical formulation is non-toxic and does not irritate the animal's skin.

In a preferred embodiment of the invention, the volume of total insecticide formulation applied onto a companion pet is in the range of about 0.5 to 10 ml, preferably about 2 to 5 ml, and most preferably, about 3 ml. In another embodiment of the invention, the volume of total insecticide formulation applied onto a small cat or kitten is in the range of about 0.5 to 1.5 ml. It should be noted that the total insecticide formulation contains solvents and other additives in addition to active ingredients and therefore, the volume of total insecticide formulation applied onto the animal does not comprise only actives.

In preferred embodiments of the invention, the dosages of active ingredients in a single application of the topical formulation comprise approximately 0.16 to 4.80 mg of a macrocyclic lactone and approximately 90 to 1350 mg dinotefuran plus solvent, and preferably approximately 0.32 to 3.2 mg of a macrocyclic lactone and approximately 180 to 900 mg dinotefuran plus solvent. In a preferred embodiment of the invention, the formulation further comprises an IGR such as pyriproxyfen or methoprene.

In embodiments of the invention where pyriproxyfen is added to the formulation, the dosage of pyriproxyfen in the total volume of a single application of the formulation is approximately 3.5 to 45 mg, and preferably, approximately 7 to 30 mg. In embodiments of the invention where methoprene is added to the formulation, the dosage of methoprene in the total volume of a single application of the formulation is approximately 10 to 135 mg, and preferably, approximately 20 to 90 mg.

The treatment of different endoparasites and ectoparasites can be targeted by including a particular macrocyclic lactone in the formulation. It should be understood that the invention is not limited by the embodiments described herein.

In a preferred embodiment of the invention, the insecticide formulation comprises ivermectin, dinotefuran and pyriproxyfen for the treatment of endoparasites and/or ectoparasites on cats and dogs. It should of course be understood that the actual amount of ivermectin in the formulation will vary depending on the size of the dog or cat. In a preferred embodiment the ivermectin ranges approximately 0.2 to 1.75 mg per ml of formulation.

In one embodiment of the invention, up to 8 ml of the total insecticide composition can be administered to a dog weighing 55 to 120 pounds, and preferably, up to 6 ml. Such composition will preferably comprise at least about 1.6 to 4.8 mg of ivermectin, at least about 450 to 1350 mg dinotefuran, and at least about 15 to 45 mg of pyriproxyfen. Even more preferably, the composition will comprise approximately 3.2 mg of ivermectin, approximately 900 mg dinotefuran, and approximately 30 mg of pyriproxyfen. In embodiments where the IGR is methoprene, the composition comprises at least about 45 to 180 mg methoprene. In another preferred embodiment of the invention, approximately 6 to 8 ml of the total composition can be administered to a 55 to 120 lb dog, which advantageously comprises approximately 675 to 2025 mg of permethrin or approximately 2015 to 5050 mg of phenothrin in order to provide additional acaricide efficacy and to repel and kill mosquitoes.

In one embodiment of the invention, up to 4 ml of insecticide can be administered to a dog weighing 22 to 55 pounds. Such composition will preferably comprise at least about 1.0 to 3.0 mg of ivermectin, at least about 300 to 900 mg dinotefuran, (and at least about 10 to 30 mg of pyriproxyfen. Even more preferably, the composition will comprise approximately 2.0 mg of ivermectin, approximately 600 mg dinotefuran, and approximately 20 mg of pyriproxyfen. In embodiments where the IGR is methoprene, the composition comprises at least about 30 to 90 mg methoprene. In another preferred embodiment of the invention, the composition further comprises approximately 450 to 1350 mg of permethrin or approximately 1115 and 3345 mg of phenothrin in order to provide additional acaricide efficacy and to repel and kill mosquitoes.

In one embodiment of the invention, up to 2.1 ml of insecticide can be administered to an animal weighing 9 to 22 pounds. Such composition will preferably comprise at least about 0.4 to 1.2 mg of ivermectin, at least about 225 to 675 mg dinotefuran, and at least about 5 to 15 mg of pyriproxyfen. Even more preferably, the composition will comprise approximately 0.8 mg of ivermectin, approximately 450 mg dinotefuran, and approximately 10 mg of pyriproxyfen.

In another preferred embodiment, the composition further comprises at least about 225 to 675 mg permethrin or about 560 to 1675 mg phenothrin in order to provide additional acaricide efficacy and to repel and kill mosquitoes. It should be noted that formulations containing permethrin are for application to dogs only. In embodiments where the IGR is methoprene, the composition comprises at least about 15 to 45 mg methoprene.

In one embodiment of the invention, up to 1.5 ml of insecticide can be administered to animals weighing 9 pounds or less. Such composition will preferably comprise at least about 0.15 to 0.60 mg of ivermectin, at least about 90 to 270 mg dinotefuran, and at least about 3.5 to 12 mg of pyriproxyfen. Even more preferably, the composition will comprise approximately 0.32 mg of ivermectin, approximately 180 mg dinotefuran, and approximately 7 mg of pyriproxyfen. In embodiments where the IGR is methoprene, the composition comprises at least about 10 to 30 mg methoprene. In another preferred embodiment, the composition further comprises at least about 150 to 450 mg permethrin or about 475 to 1425 mg phenothrin in order to provide additional acaricide efficacy and to repel and kill mosquitoes. It should be noted that formulations containing permethrin are for application for dogs only.

In another preferred embodiment of the invention, the insecticide formulation comprises selamectin, dinotefuran and pyriproxyfen for the treatment of endoparasites and/or ectoparasites on cats and dogs. It has been determined that an effective dosage for selamectin contained in insecticide formulations according to the invention is approximately 3 to 6 mg per pound of animal body weight. Therefore, the actual amount of selamectin in the insecticide formulation will vary depending on the size of the dog or cat (for example, approximately 30 to 210 mg per ml of formulation).

In a preferred embodiment of the invention, the insecticide formulation comprises moxidectin, dinotefuran and pyriproxyfen for the treatment of endoparasites and/or ectoparasites on cats and dogs. It has been determined that an effective dosage for moxidectin contained in insecticide formulations according to the invention is approximately 0.2 mg per pound of animal body weight. Therefore, the actual amount of moxidectin in the insecticide formulation will vary depending on the size of the dog or cat.

In another preferred embodiment of the invention, the insecticide formulation comprises doramectin, dinotefuran and pyriproxyfen for the treatment of endoparasites and/or ectoparasites on cats and dogs. It has been determined that an effective dosage for doramectin contained in insecticide formulations according to the invention is approximately 0.02 mg per pound of animal body weight. Therefore, the actual amount of doramectin in the insecticide formulation will vary depending on the size of the dog or cat.

In the preparation of a formulation for use on animals, there are several parameters that should be considered. These are:
   (a) Concentration high enough to minimize the volume of the topical applied to the animal (one would not want to put 20 ml, e.g., onto a small dog).
   (b) Concentration low enough to achieve effective translocation of the topical insecticide over the animal's skin.
   (c) The formulation should be stable for six months at 40° F. and 75% relative humidity, room temperature and −10° F. This helps ensure that the formulation remains stable under the conditions that it could meet in commerce.
   (d) Safe to use on the intended animal—particularly non-irritating to at least the intended animal, since the product is applied to the skin. Also safe if ingested by the animal; ingestion can occur when pets groom themselves.
   (e) Safe to use by the consumer.
   (f) Efficacious in use—should kill greater than 90% of the fleas and ticks up to 28 days and kill or eliminate the endoparasites.
   (g) Efficacy would be reduced if crystallization occurred in the package.
   (h) Needs to be aesthetically pleasing—"no oily drop" on the animal when applied.
   (i) Fast drying to reduce the chance of the animal shaking off the liquid thereby reducing efficacy.
   (j) Microbiologically stable.

It can be advantageous for the insecticidal formulations of the invention to contain an enzyme inhibitor or a synergist such as piperonyl butoxide, N-octylbicycloheptenedicarboximide, or triphenyl phosphate, which can increase the efficacy of the formulation. The topical formulations also contain one or more compounds to increase the efficacy and to reduce the irritation of pyrethroid insecticides to the skin of animals. The formulation can advantageously contain spreading agents such as n-octyl pyrrolidone and dioctylsulfosuccinimide, fragrances, and/or antioxidants.

Other additives to the insecticidal composition include but are not limited to fragrances, surfactants and spreading agents to increase performance such as polyoxyethylene (20) sorbitan monolaurate (commerically available as polysorbate 20 or Tween® 20) and polyoxyethylene (20) sorbitan monooleate (commerically available as polysorbate 80 or Tween® 80), and isopropyl myristate. Polymers such as agar, gelatin, alginate, and cationic polymers such as cationic guar, cationic cellulose, cationic acrylates, and polyoxymethylene urea may also be added to provide enrobing of the insecticide to improve safety and adhesion to skin and hair.

In practice, an effective amount of the insecticidal compositions as described herein may be applied to a companion animal, preferably a dog or a cat, as a foaming shampoo, dip, aerosol spray, pump spray, powder, lotion, emulsifiable concentrate, aqueous or liquid flowable, suspension concentrate and by any other methods suitable for administering topical compositions to animals. Formulations containing permethrin cannot be applied to cats.

The following examples are given for purposes of illustration only and are not intended to be construed in a limiting manner.

EXAMPLES

Example 1

Preparation of 1-[(tetrahydro-3-furanyl)methyl]-2-nitro-3-methylguanidine (dinotefuran)

A mixture comprising 10.0 g of (tetrahydro-3-furanyl) methanol, 29.5 g of trifluoromethanesulfonic anhydride, 10.0 g of pyridine and 200 ml of dichloromethane was stirred for an hour at room temperature. Water was poured into the reaction solution to separate the organic layer, which was washed with 1 N hydrochloric acid, water and a saturated saline solution, dried, and concentrated to obtain 20 g of 3-tetrahydro-furanylmethyl triflate. 3.25 g of 60% sodium hydride were added to 12.5 g of 1,5-dimethyl-2-nitroiminohexahydro-1,3,5-triazine and 60 ml of DMF at room temperature, followed by stirring for an hour. 20.0 g of the 3 tetrahydrofuranylmethyl triflate were added thereto, and the mixture was stirred at 50° C. for 2 hours. After cooling the mixture to room temperature, 50 ml of 2N hydrochloric acid were added thereto, followed by stirring at 50° C. for 2 hours. The resultant mixture was neutralized with sodium bicarbonate and extracted with dichloromethane, and the extract was dried and concentrated. The residue thus obtained was purified by silica gel column chromatography (eluent: ethyl acetate/hexane=1/1) to obtain 7.8 g of 1-{(tetrahydro-3-furanyl)methyl}-2-nitro-3-methylguanidine (dinotefuran).

Example 2

Ivermectin/Dinotefuran Formulations

Ivermectin (0.05 g) was dissolved in ethanol in a clean container with stirring until it was completely dissolved. This solution was added to a chamber in the package in the appropriate volume based on the dosage required.

A second solution containing dinotefuran was prepared by adding 25 g of dinotefuran to 100 ml phenyl methanol with stirring until it dissolved. This solution was added to the other chamber in the package in the appropriate volume based on the dosage required.

Example 3

Preparation of Compositions Containing Ivermectin, Dinotefuran and Pyriproxyfen A solution containing ivermectin was prepared using the methodology of Example 2 and placed in a chamber in the package in the appropriate volume based on the dosge required.

Pyriproxyfen (1 g) and Mackernium KP (1 g) were added to a clean container, and gently heated until the pyriproxyfen liquefied. Water (27.6 g) was added with stirring, followed by the addition of ethyl lactate (55.4 g). Dinotefuran (15 g) was added and the solution was mixed and heated at 50 degrees C. until the dinotefuran dissolved. The solution was cooled to room temperature and the pH adjusted to 5.5 by the addition of sodium carbonate (0.15 g of a 25% aqueous solution). This solution was added to the other chamber in the package in the appropriate volume based on the dosage required.

Example 4

Preparation of Compositions Containing Ivermectin, Dinotefuran and Methoprene A solution containing ivermectin was prepared using the methodology of Example 2 and placed in a chamber in the package in the appropriate volume based on the dosage required.

Methoprene (1 g) and Mackernium KP (1 g) were added to a clean container, and gently heated. Water (27.6 g) was added with stirring, followed by the addition of ethyl lactate (55.4 g). Dinotefuran (15 g) was added and the solution was mixed and heated at 50 degrees C. until the dinotefuran dissolved. The solution was cooled to room temperature and the pH adjusted to 5.5 by the addition of sodium carbonate (0.15 g of a 25% aqueous solution). This solution containing dinotefuran and methoprene was added to the other chamber in the package in the appropriate volume based on the dosage required.

Example 5

Preparation of Compositions Containing Ivermectin Dinotefuran, Permethrin and Pyriproxyfen Permethrin (6.5 g) was dissolved in ethanol in a clean container with stirring. Ivermectin (0.05 g) was added to this solution with stirring until it was completely dissolved. Permethrin or phenothrin is preferably added to insecticide formulations according to the present invention in order to kill ticks and repel flies and mosquitoes. This solution containing permethrin and ivermectin was added to one of the chambers in the package in the appropriate volume based on the dosage required.

Pyriproxyfen (1 g) and Mackernium KP (1 g) were added to a clean container, and gently heated until the pyriproxyfen liquefied. Water (27.6 g) was added with stirring, followed by the addition of ethyl lactate (55.4 g). Dinotefuran (15 g) was added and the solution was mixed and heated at 50 degrees C. until the dinotefuran dissolved. The solution was cooled to room temperature and the pH adjusted to 5.5 by the addition of sodium carbonate (0.15 g of a 25% aqueous solution). This solution was added to the other chamber in the package in the appropriate volume based on the dosage required.

Example 6

Preparation of Compositions Containing Ivermectin Dinotefuran Phenothrin and Pyriproxyfen Phenothrin (6.5 g) was dissolved in ethanol in a clean container with stirring. Ivermectin (0.05 g) was added to this solution with stirring until it was completely dissolved. Permethrin or phenothrin is preferably added to insecticide formulations according to the present invention in order to kill ticks and repel flies and mosquitoes. This solution containing phenothrin and ivermectin was added to one of the chambers in the package in the appropriate volume based on the dosage required.

Pyriproxyfen (1 g) and Mackernium KP (1 g) were added to a clean container, and gently heated until the pyriproxyfen liquefied. Water (27.6 g) was added with stirring, followed by the addition of ethyl lactate (55.4 g). Dinotefuran (15 g) was added and the solution was mixed and heated at 50 degrees C. until the dinotefuran dissolved. The solution was cooled to room temperature and the pH adjusted to 5.5 by the addition of sodium carbonate (0.15 g of a 25% aqueous solution). This solution was added to the other chamber in the package in the appropriate volume based on the dosage required.

Example 7

Moxidectin/Dinotefuran Compositions

In a preferred embodiment of the invention, an insecticide formulation containing moxidectin and dinotefuran was prepared using the methodology described in Example 3.

Preferably, the total volume of the formulation is approximately 6 ml, comprises 11 to 24 mg of moxidectin and approximately 15% dinotefuran, which is approximately 900 mg dinotefuran for the treatment and prevention of fleas, prevention of heartworm, the control of roundworm, hookworms, and whipworms in dogs and cats. As used herein, it is to be understood that the prevention of a specific parasite implies that the active ingredient precludes the parasite from having an effect, i.e., the active ingredient prevents the parasites from infesting the animal because the parasites are killed as soon as they enter the animal. Furthermore, it is to be understood that controlling a parasites implies that the active ingredient kills the parasites in an already infested animal.

Preferably, the formulation further comprises approximately 10 mg/ml pyriproxyfen or approximately 30 mg/ml methoprene to kill flea larvae and prevent flea eggs from hatching. Even more preferably, the formulation also includes permethrin or phenothrin to kill ticks and repel mosquitoes and flies.

Example 8

Selamectin/Dinotefuran Compositions

In yet another preferred embodiment of the invention, an insecticide composition containing selamectin and dinotefuran was prepared using the methodology described in Example 2.

Preferably, the total volume of the formulation applied to the companion animal is approximately 6 ml, which comprises approximately 8% to 15% dinotefuran and 2.6 to 12% selamectin. In a preferred embodiment of the invention, the formulation comprises approximately 480 to 900 mg dinotefuran and 155 to 720 mg selamectin dissolved in solvent, which is effective in killing fleas, preventing flea eggs from hatching, preventing heartworm, controlling and treating ear mites, sacroptic mange and controlling tick infestation due to *Dermacentor variabilis* in dogs. The formulation advantageously further comprises approximately 60 mg (10 mg/ml) pyriproxyfen or approximately 180 mg (30 mg/ml) methoprene, which provides additional efficacy against flea eggs.

Example 9

Compositions Containing Selamectin, Dinotefuran Permethrin and Pyriproxyfen

In another embodiment of the invention, permethrin (489.1 g) was dissolved in safflower oil (435.9 g) in a clean container with stirring. Selamectin (75 g) was added to this mixture with stirring until it was completely dissolved. Permethrin or phenothrin is preferably added to insecticide formulations according to the present invention for additional acaricide efficacy and for the treatment of mosquitoes and flies. This solution containing permethrin and selamectin was added to one of the chambers in the package in the appropriate volume based on the dosage required.

Pyriproxyfen (1.5 g) and Mackernium KP (1 g) were added to a clean container, and gently heated until the pyriproxyfen liquefied. Water (22.7 g) was added with stirring, followed by the addition of ethyl lactate (47.8 g). Dinotefuran (15 g) was added and the solution was mixed and heated at 50 degrees C. until the dinotefuran dissolved. The solution was cooled to room temperature and the pH adjusted to 5.5 by the addition of sodium carbonate (0.15 g of a 25% aqueous solution). This solution was added to the other chamber in the package in the appropriate volume based on the dosage required.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following embodiments are intended to cover all of the generic and specific features of the invention herein described and all statements of the scope of the invention which, as a matter of language, might be said to fall therebetween.

Particularly it is to be understood that in said embodiments, ingredients or compounds recited in the singular are intended to include compatible mixtures of such ingredients wherever the sense permits.

What is claimed is:

1. A topical formulation comprising a first active ingredient comprising approximately 0.2 to 1.75 mg ivermectin per ml of total volume of formulation and a second active ingredient comprising 50 to 150 mg dinotefuran per ml of total volume of formulation, wherein the formulation further comprises (I) permethrin or phenothrin and (ii) an insect growth regulator comprising pyriproxyfen or methoprene, and wherein the first active ingredient and the second active ingredient are packaged with said permethrin or phenothrin, but isolated from interacting with said permethrin or phenothrin.

2. The topical formulation of claim 1, wherein the active ingredients are isolated via the use of granulation, encapsulation, micelles, or encapsulated microbeads.

3. The topical formulation of claim 1, wherein the formulation is not irritating to cats and dogs and is effective to kill endoparasites and ectoparasites with applications of less than 10 ml.

4. A method for treating endoparasitic or ectoparasitic infestation in an animal, the method comprising applying the topical formulation of claim 1 to the animal.

5. The method of claim 4 wherein the animal is a cat or a dog.

6. A topical formulation comprising a first active ingredient comprising approximately 0.2 to 1.75 mg ivermectin per ml of total volume of formulation and a second active ingredient comprising 50 to 150 mg dinotefuran per ml of total volume of formulation, wherein the formulation further comprises (i) permethrin or phenothrin and (ii) an insect growth regulator comprising pyriproxyfen or methoprene, wherein the ivermectin and dinotefuran are packaged in a first container, permethrin or phenothrin is packaged in a second container, and the insect growth regulator is packaged in either the first container or the second container, the first container. packaged in a manner in which it is separated from the second container, in order to prevent interaction with the second container prior to administrating the topical formulation.

7. The topical formulation of claim 6, wherein the first and second containers are packaged together but separated by at least one barrier to prevent the interaction of the first container with the second container.

8. The topical formulation of claim 6, wherein the formulation is not irritating to cats and dogs and is effective to kill endoparasites and ectoparasites with applications of less than 10 ml.

9. A method for treating endoparasitic or ectoparasitic infestation in an animal, the method comprising applying the topical formulation of claim 6 to the animal.

10. The method of claim 4, wherein the animal is a cat or dog.

* * * * *